United States Patent [19]
Sudo et al.

[11] Patent Number: 5,594,246
[45] Date of Patent: *Jan. 14, 1997

[54] METHOD AND APPARATUS FOR X-RAY ANALYSES

[75] Inventors: Yoshimi Sudo, Hachioji; Tokuo Kure, Tokyo; Ken Ninomiya, Higashi-Matsuyama; Katsuhiro Kuroda, Hachioji; Takashi Nishida; Hideo Todokoro, both of Tokyo; Yasuhiro Mitsui, Fuchu; Hiroyasu Shichi, Tanashi, all of Japan

[73] Assignee: Hitachi, Ltd., Tokyo, Japan

[*] Notice: The term of this patent shall not extend beyond the expiration date of Pat. No. 5,481,109.

[21] Appl. No.: 430,535

[22] Filed: Apr. 25, 1995

Related U.S. Application Data

[63] Continuation-in-part of Ser. No. 211,575, Apr. 11, 1994, Pat. No. 5,481,109.

[30] Foreign Application Priority Data

Apr. 28, 1994 [JP] Japan .................................. 6-091034

[51] Int. Cl.$^6$ ....................... H01J 37/252; G01N 23/223; G01N 23/225
[52] U.S. Cl. ........................... 250/310; 250/397; 250/307
[58] Field of Search ................................. 250/310, 397, 250/307

[56] References Cited

U.S. PATENT DOCUMENTS

| | | | |
|---|---|---|---|
| 4,570,072 | 2/1986 | Kimura et al. | 250/397 |
| 4,697,080 | 9/1987 | King | 250/310 |
| 5,481,109 | 1/1996 | Ninomiya et al. | 250/310 |

FOREIGN PATENT DOCUMENTS

| | | |
|---|---|---|
| 55-3129 | 1/1980 | Japan . |
| 63-243855 | 10/1988 | Japan . |

OTHER PUBLICATIONS

Optical Systems for Soft X–Rays, Alan Michette, pp. 17–23 No date.

*Primary Examiner*—Jack I. Berman
*Attorney, Agent, or Firm*—Fay, Sharpe, Beall, Fagan, Minnich & McKee

[57] ABSTRACT

An X-ray analyzing method includes the steps of applying an irradiated electron beam, converged by a condenser lens and an objective lens into a thin beam, to the inside of a fine hole existing on the surface of a sample; observing X-rays generated from a residual substance existing inside the fine hole; and performing a qualitative and quantitative analysis of the residual substance. The X-rays are observed by an X-ray detector installed in an internal space of the condenser lens, an internal space of the objective lens, or between the condenser lens and the objective lens, by detecting only the X-rays radiated within the angular range $-\theta$ to $+\theta$, where $\theta$ is an angle formed with a center axis of the electron beam, and so defined that $\tan \theta$ is substantially equal to $a/d$, where a and d are the radius and the depth of the fine hole, respectively.

75 Claims, 10 Drawing Sheets

$\tan \theta = a/d$ $\tan \theta = a/d$

METHOD AND APPARATUS FOR X-RAY ANALYSES

CROSS-REFERENCE TO RELATED APPLICATION

The present invention is a continuation-in-part of application Ser. No. 08/211,575 filed on Apr. 11, 1994, now U.S. Pat. No. 5,481,109, which is incorporated by reference herein in its entirety.

BACKGROUND OF THE INVENTION

The present invention relates to a surface-analysis technique in in particular and to an X-ray analysis method and apparatus for analyzing residue on the surface of a specimen or sample.

In order to promote the large-scale integration of semiconductor devices, it is necessary to establish a fine-line patterning process technology at a level smaller than the deep submicron. In the manufacturing of 1-Gb DRAMs (Dynamic Random-Access Memories), for example, a patterning process of a contact hole having a diameter of 0.16 μm and a depth of 2 μm is required. In order to establish such a fine-line patterning process, technologies of analysis for measuring and inspecting the accuracy of the fine-line patterning are necessary. In particular, technologies of analysis that can be used for analyzing the composition and thickness of residue are required. In this residue analysis, the surface of the sample (wafer) is not necessarily flat, so that areas having large steps, such as a small contact hole described earlier, also need to be analyzed as well.

The conventional residue analysis for analyzing areas having large steps is carried out by destroying a fabricated wafer and observing the cross section of the destructed wafer by means of an SEM (Scanning Electron Microscope). With this technique, however, the composition of the residue cannot be identified only by observation of the shape and, additionally, the wafer cannot be returned to the manufacturing process after the analysis once the wafer has been deconstructed. Other problems with this technique include the fact that it is difficult to observe a trace of residue of the order of few nm. In the development of semiconductor integrated-circuit devices beyond the Gb range, the above problems which entail deterioration of the yield and the precision of analysis are regarded as fatal problems.

On the other hand, an X-ray analysis method, which is an analysis technique allowing analyses to be done without destroying a wafer, is available. An example of a typical X-ray analysis method is the use of charged-particle analysis equipment disclosed in Japanese Patent Laid-open No. Sho 63-243855. With this charged-particle analysis equipment an electron beam is applied to the surface of a sample. An X-ray generated from the surface of the sample due to the application of the electron beam is then observed. The X-ray is observed by means of a light splitting crystal placed at an angle of about 22 degrees from the center axis of the electron beam.

In order to carry out qualitative and quantitative analyses on residue by using X-rays, the place at which a means for observing the X-rays is installed is important. Specifically, in order to prevent the X-rays generated by the surface of the sample from being absorbed by an obstacle, the means for observing the X-rays must be placed at a location where no such obstacle exists. Unfortunately, however, there has been so far no clear standard concerning the location for installing a means for observing the X-rays, and little attention has hence been paid to such an installation position. In the case of the charged-particle analysis equipment mentioned above, a light splitting crystal is positioned at an angle of 22 degrees. Nonetheless, the absorption of the X-rays cannot be avoided in some cases. In particular, in the case of large-scale integrated memories beyond the 4-Mb DRAM which are considered to be the main semiconductor devices of the future, by merely using the charged-particle analysis equipment, it will be impossible to perform qualitative and quantitative analyses of residue on the surface of a sample.

SUMMARY OF THE INVENTION

It is an object of the present invention to provide an X-ray analysis method and apparatus which can be used for carrying out qualitative and quantitative analyses of residue on the surface of a sample with a high degree of sensitivity without destroying the sample.

In order to achieve the object, the present invention provides an electron-beam irradiating means for irradiating and focusing a low acceleration electron beam and applying the electron beam to the surface of a sample, and an X-ray observing mean for observing an X-ray generated by the surface of the sample due to the application of the electron beam from a position in a direction close to the irradiated electron beam.

When an irradiated electron beam is applied to a substance, X-rays are generated by the substance. The energy (or wavelength) of the generated X-rays is an inherent quantity of the element mating up the substance. Accordingly, the element and, hence, the substance, can be identified by analysis is known as a the generated X-rays. Such an analysis is known as a qualitative analysis. In addition, information on the quantity of the substance (or the film thickness) can be obtained from the intensity of the irradiated X-rays. An analysis that results in information on the film thickness is called a quantitative analysis.

In order to allow an analysis to be performed on residue even on areas having large steps without destroying the sample (or wafer), a method of observing an X-ray generated from the surface of the sample is important. There are two types of main residue in a process of manufacturing semiconductor devices: a silicon oxide film and a photoresist layer. In order to identify components of these residues, X-rays generated by light elements such as the C (carbon), O (oxygen) and Si (silicon) atoms must be detected. The amount of energy of a CK α X-ray or an OK α X-ray generated by the application of an irradiated electron beam to a substance has a small value of less than 1 keV. Accordingly, such an X-ray cannot pass through an obstacle which may exist, if any, between a location generating the X-ray and a means for observing the X-ray. As a result, the X-ray cannot be observed. Although X-rays may pass through an obstacle in general, most X-rays are so absorbed by the obstacle as to be unable to be detected. The state of X-ray observation is described in more detail below by citing an example of an analysis of residue inside a fine hole which must be carried out under most severe observation conditions. An example of a fine hole is the contact hole mentioned earlier.

FIG. 2 shows an incident electron beam 1 entering a fine hole H on the surface of a sample 2. As described previously, a generated X-ray 5 must be observed from a position in a direct where no obstacle exists between the location generating the X-ray and the observation means. Namely, it is necessary to observe the X-rays 5 from a position in an area A in FIG. 2 covering what is referred to hereafter as directions close to the electron beam. Here, an angle θ is so defined that tan θ is equal to a/d, where a and d are the radius add the depth of the fine hole H respectively. In the case that the X-rays which pass through an obstacle are strong enough to be detected, the angle θ becomes slightly larger than arctan(a/d). The attenuations of the X-rays during passing through an obstacle depend not only on the energy of the X-rays and the elements included in the obstacle, but dominantly on the transmission distance of the X-rays inside the obstacle. That is, the angle θ may be defined that tan θ is substantially equal to a/d.

When considering large-scale integration of future semiconductor devices such as memory products beyond the 4-Mb DRAM, it is necessary to observe X-rays generated by a contact hole from a position on a direction that forms, with the electron beam, a θ angle of smaller than 20 degrees. In the charged-particle analysis equipment disclosed in Japanese Patent Laid-open No. Sho 63-243855 cited previously, a light splitting crystal for observing generated X-rays is located at a position in a direction forming a θ angle of 22 degrees with the center axis of the electron beam. Accordingly, the charged-particle analysis equipment cannot be applied to the analysis of residue in a contact hole of a device beyond the 4-Mb DRAM. In contrast to this equipment, a means provided by the present invention for observing X-rays includes an X-ray detector, and a detecting surface which is partially or completely located in an area with a θ angle cited above of smaller than 20 degrees or the area A shown in FIG. 2, or to include an optical device partially or totally located in the area A for leading the X rays to the X-ray detector. A variety of techniques can be thought of as a means for observing an X-ray. These techniques are explained one after another through the following detailed description of preferred embodiments.

As described above, by applying an irradiated electron beam to the surface of a sample and observing X-rays generated by the surface from a position in a direction close to the electron beam, qualitative and quantitative analyses can be carried out on residue on the surface of a sample with large steps such as contact holes, to say nothing of a sample with small steps.

These and other objects and any of the attendant advantages of the present invention will be readily appreciated as the same becomes better understood by reference to the following detailed description when considered in connection with the accompanying drawings.

DETAILED DESCRIPTION OF THE PREFERRED EMBODIMENTS

The present invention will become apparent from the following detailed description of preferred embodiments with reference to the accompanying diagrams.

Embodiment 1

Figure 1:
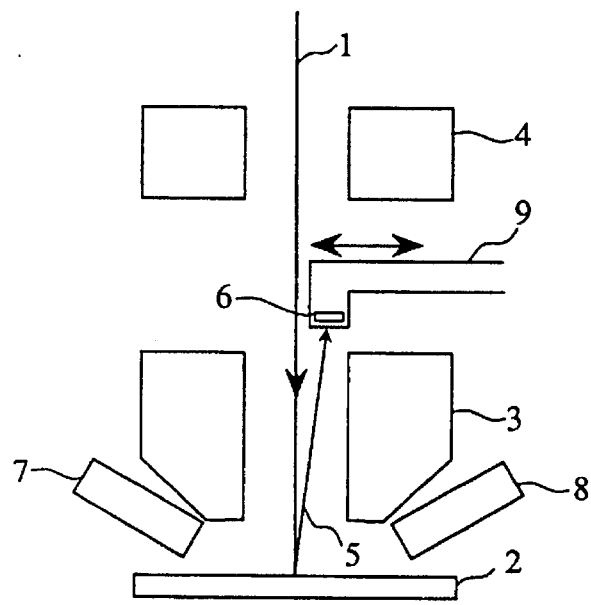
FIG. 1 is a cross-sectional model diagram showing a simplified configuration of an embodiment implementing an X-ray, analysis apparatus in accordance with the present invention.

A most basic embodiment of the present invention is shown in FIG. 1. As shown in the figure, an accelerated electron beam 1 is applied perpendicularly to the surface of a sample 2. Here, the electron beam 1 is converged so that the diameter of the beam is decreased to a sufficiently small value in comparison with the size of a deposition region of residue on the surface of the sample 2 to be analyzed. An example of the size of such a deposition region is the diameter of a fine hole. In this way, the accelerating energy of the electron beam i is controlled to a value smaller than 5 keV. The electron beam i is converged by means of an objective lens 3 and a condenser lens 4.

The application of the irradiated electron beam 1 to the surface of the sample 2 causes an X-ray 5 to be generated by the residue on the surface of the sample 2. The X-ray 5 is detected by a detector 6 installed at a position in a direction close to the electron beam 1 between the objective lens 3 and the condenser lens 4. Having an energy analyzing function, a representative detector 6 includes an X-ray solid-state detector and a parpicon (imaging tube).

Figure 2:
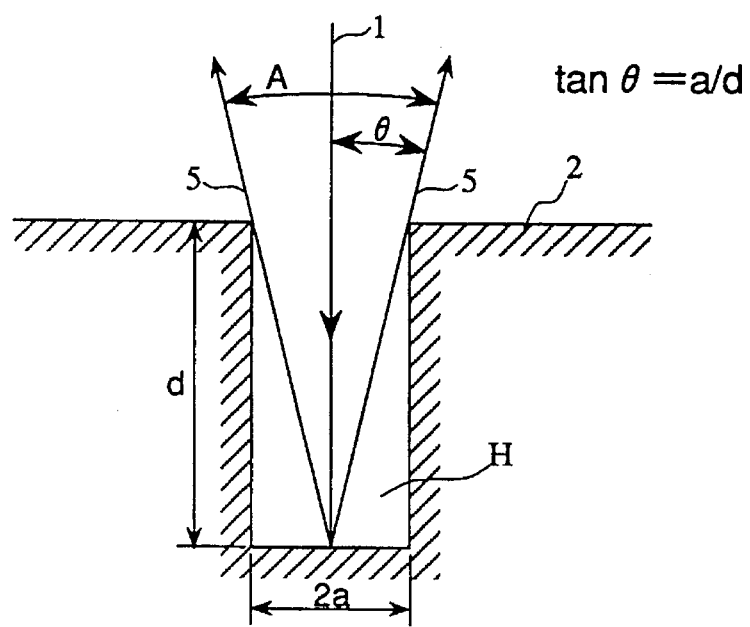
FIG. 2 is a cross-sectional model diagram used for explaining a position at which an X-ray detector is installed.

A significant point to be taken into consideration in the installation of the detector 6 is that the detector 6 must be installed so that a surface thereof for detecting the X-ray 5 is partially or completely located inside the area A shown in FIG. 2. In order to install the detector 6 in this way, it is thus necessary to place the detector 6 at a position as close as possible to the electron beam 1 so as to make the gap between the detector 6 and the electron beam 1 have a value of the order of 1 mm. Therefore, it is essential to converge the electron beam 1 into a sufficiently thin beam so that it goes not hit the detector 6. By measuring the energy and the intensity of the X-ray 5 by means of the detector 6, a qualitative and quantitative analysis of the residue can be carried out.

A high-energy X-ray such as the SiK α X-ray can penetrate a substance with a thickness of the order of several μm. Such a high-energy X-ray can be detected even by a detector 7 installed beside the unit that irradiates the electron beam. Again, this detector 7 can be an X-ray solid-state detector or the like which has an energy analyzing function. By comparing signal intensities detected by the detectors 6 and 7, the attenuation factor of an X-ray passing through a substance can be obtained. From the attenuation factor, the thickness of the substance can, in turn, be derived. By using this information, it is possible to find, for example, the depth of a fine hole on the surface of the sample 2.

The application of the electron beam 1 to the surface of the sample 2 also causes secondary electrons to be generated therefrom as well. A secondary-electron detector 8 is provided for detecting the secondary electrons. By detecting secondary electrons while scanning the electron beam 1 over the surface of the sample 2, a secondary-electron image can be obtained. By making use of the secondary-electron image, information on the position of residue can be obtained with ease and the position can also be set easily.

The detector 6 is installed in a housing 9 which can be moved in a direction denote by an arrow in the figure. This scheme allows the distance from the housing 9 to the electron beam 1 to be kept constant all the time even in the case of an X-ray analysis conducted by varying the accelerating voltage and converging conditions of the electron beam 1.

In a qualitative and quantitative analysis of a residual substance existing on the bottom surface of a fine hole such as a contact hole through detection of an X-ray generated by application of an irradiated electron beam to the residual substance, an X-ray observing means must be installed at a position above the fine hole close to the center axis of the irradiated electron beam so that area on the bottom surface of the fine hole generating the X-ray can be viewed directly, in order to avoid absorption of the generated X ray by the sidewall of the fine hole. When positioning the X-ray observing means close to the center axis of the electron beam, it is necessary to exercise caution so as to prevent the X-ray observing means from having a deleterious effect on the irradiated electron beam. For this reason, it is desirable to make up components which constitute the X-ray detector 6 from a non-magnetic material such as aluminum, copper or stainless steel completing demagnetization treatment. In addition, in the case of an X-ray detector 6 enclosed in a housing 9 as described earlier, it is likewise desirable to make up at least components on the side of the X-ray detector 6 facing the electron beam 1 including the housing 9 from the non-magnetic material described above.

Figure 12:
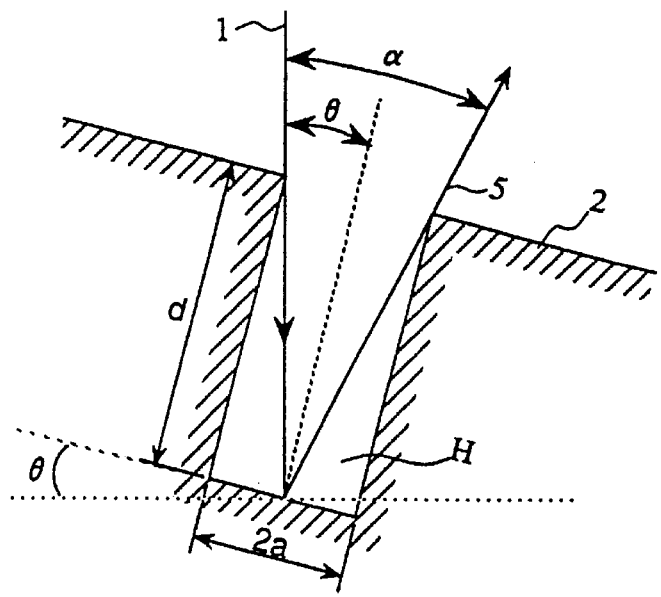
FIG. 12 is a cross-sectional model diagram used for explaining a position at which an X-ray detector is installed in the case of a slanting sample.

FIGS. 1 and 2 show configurations in which the electron beam 1 is applied perpendicularly to the bottom surface of the sample 2. By slanting the sample 2, the permissible range of angles at which the X-ray generated from the bottom surface of the fine hole is detected can be increased. Let, for example, the sample 2 be slanted from the horizontal direction by an angle θ as shown in FIG. 12. It should be noted that θ has previously been so defined that tan θ is equal to a/d, where a and d are the radius and the depth of the fine hole, respectively. In this case, an angle α at which the X-ray can be observed from a position above the fine hole without being obstructed by the sidewall of the fine hole is equal to 2×θ, resulting in a permissible range of angles of detection twice as much that with the sample 2 not slanting. In this way, by slanting the surface of the sample 2 relatively to the irradiated electron beam 1, the permissible range of angles for detecting the X-ray can be widened, allowing the sensitivity of the X-ray detection to be increased accordingly. Moreover, the X-ray can be observed with ease.

Figure 13:
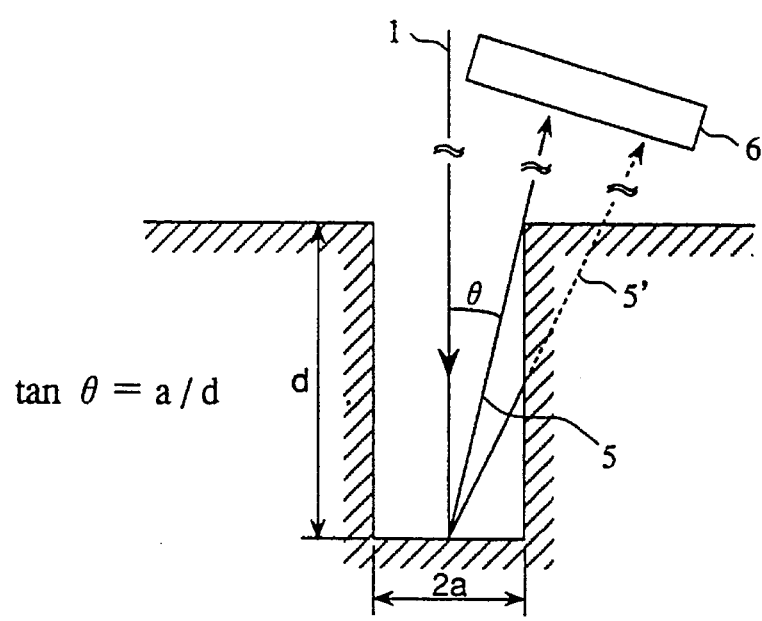
FIG. 13 is a cross-sectional model diagram used for explaining the state of an X-ray arriving at a detector after passing through a sample.

It should be noted that the permissible range of angles formed with the center axis of the electron beam at which the X-ray is observed is not necessarily limited to the ranges of angles θ and α shown in FIGS. 2 and 12 respectively. As shown in FIG. 13, X-rays generated from the bottom surface of the fine hole by the application of an irradiated electron beam thereto also include an X-ray 5' penetrating the sidewall of the fine hole before arriving at the detector 6, in addition to an X-ray 5 which arrives at the detector 6 without being obstructed by the sidewall of the fine hole. In this case, the transmission rate of the penetrating X-ray 5' has a variable value depending upon the material of which the sidewall of the fine hole is made, the type (or the energy) of the X-ray, or the hole size (that is, the diameter and depth) of the fine hole.

Figure 14:
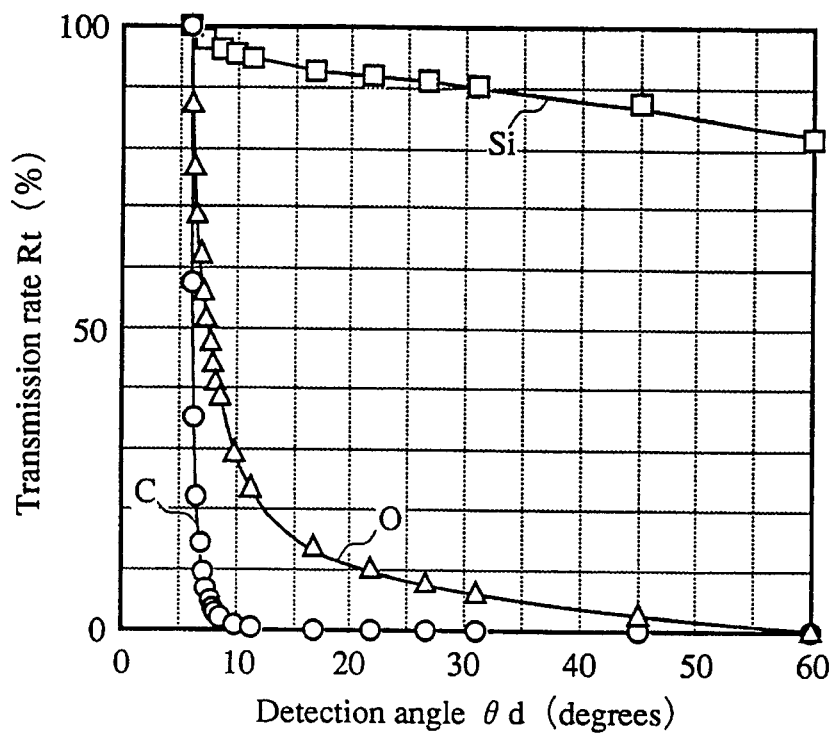
FIGS. 14 and 15 are diagrams curves representing relations between the angle of detection of the X-ray shown in FIG. 13 and the transmission rate.

Let, for example, the material of the sidewall be a resist film as is the case with a contact hole of a semiconductor device. In this case, dependence of the transmission rate $R_t$ of the X-ray generated from an element such as C (carbon), O (oxygen) or Si (silicon) cited earlier on the angle of detection ($θ_d$) formed with the center axis of the irradiated electron beam is shown in FIG. 14. The transmission rate $R_t$ is the rate at which an X-ray penetrates the resist-film sidewalk, arriving at the detector 6 is meant. It should be noted that the figure shows dependence for the following hole dimensions: a hole diameter (2a) of 0.2 μm, a depth (d) of 1 micrometer and an aspect ratio d/2a of 5.0. In this case, the angle θ is previously so defined that tan θ is equal to a/d which is 5.71 degrees.

It is obvious from the figure that a carbon X-ray is almost entirely absorbed as soon as it enters the resist film. For an angle of detection $θ_d$ exceeding the angle θ (=5.71 degrees) the carbon X-ray cannot thus be observed. As a result, the angle of detection $θ_d$ must be smaller than the angle θ in order for the carbon X-ray to be able to arrive at the detector 6.

On the other hand, an oxygen X ray passes through the resist film at a transmission rate of about 10% and is hence able to arrive at the detector 6 even if the angle of detection is set at 20 degrees. As for a silicon X-ray, the rate of absorption by the resist film is very low. Accordingly, the silicon X ray passes through the resist film at a transmission rate of about 80% and is therefore able to arrive at the detector 6 even if the angle of detection is set at 60 degrees. For this reason, an X-ray having energy higher than those of silicon and aluminum can also be observed at an angle of greater than 22 degrees from the center axis of the electron beam, as is generally known.

Figure 15:
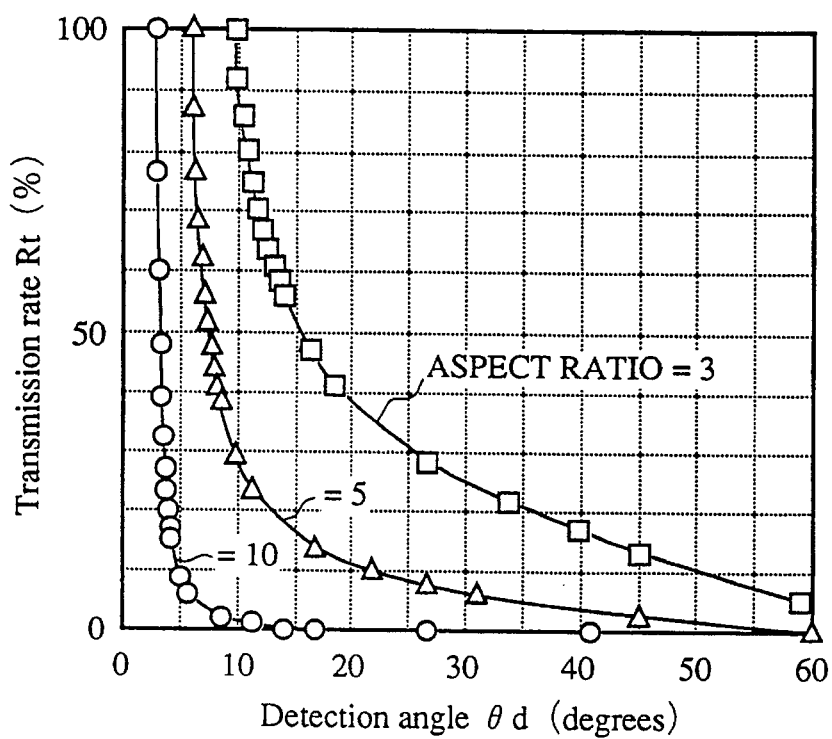

FIG. 15 shows how the transmission rate of an oxygen X-ray varies with changes in aspect ratio d/2a of a contact hole under the same conditions as those described above. It is obvious from the figure that the smaller the aspect ratio d/2a, essentially the shorter the transmission distance, defined as the distance in the sidewall of the contact hole traveled along by the oxygen X-ray which originates from an X-ray source on the bottom surface of the contact hole, penetrating the sidewall of the contact hole toward the detector 6. As a result, the transmission rate of the X-ray increases. Accordingly, when analyzing the bottom surface of a contact hole having a small aspect ratio, the analysis can then be carried out with a high degree of sensitivity by, for example, detecting all X-rays at angles of detection smaller than 20 degrees from the center axis of the irradiated electron beam.

It should be noted that, in the examples described above the sidewall of the contact hole is made of a material having a property of letting an X-ray penetrate most easily. However, it is necessary to take every caution against the fact that, in the case of a hole sidewall made of an $SiO_2$ film or other materials, the transmission rate of the X-ray is decreased. From the explanation given above, it is obvious that, by installing an X-ray detector at an angle which allows X-rays passing through the sidewall of the contact hole to be also observed as well, in some cases, the quantity of the detected signal can be increased, enabling high-sensitivity analyses. Accordingly, the position for observing an X-ray in accordance with the present invention is not limited only to the range with upper limits determined by the angle θ, which is defined such that tan θ is equal to a/d. Instead, the observation can be carried out at a position in a range of angles at which an X-ray emitted upward after passing through the sidewall of the contact hole can also be detected. Nonetheless, it is desirable to observe the X-ray at an angle smaller than 20 degrees.

By virtue of the present invention, an X-ray generated by application of an irradiated electron beam having low energy to the surface of a sample can be observed from a position in a direction close to the electron beam. Accordingly, qualitative and quantitative analyses of residue of the surface of the sample can be carried out with a high degree of sensitivity, even for a sample having large surface steps, without destroying the sample. As a result, the sample (for example, a wafer) can be returned back to the manufacturing process.

Embodiment 2

Figure 3:
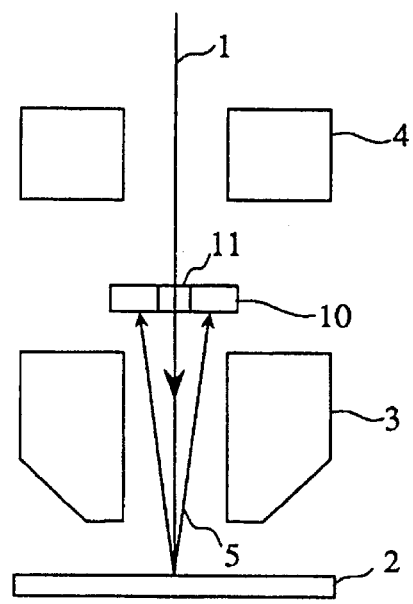
FIG. 3 is a cross-sectional model diagram showing a simplified configuration of another embodiment implementing an X-ray analysis apparatus in accordance with the present invention.

Another embodiment of the present invention is shown in FIG. 3. In this embodiment, an accelerated electron beam 1 passes through a through hole 11 at the center of a detector 10, which is installed between an objective lens 3 and a condenser lens 4. The irradiated electron beam 1 is then applied perpendicularly to the surface of a sample 2. A through hole 11 having a diameter ranging from about 0.1 to 5 mm will work. X-rays 5 generated by the application of the irradiated electron beam 1 are detected by the detector 10 to undergo energy analyses.

Since the shape of a detecting device employed in the detector 10 resembles a donut, the detection area of the detecting device can be enlarged in comparison with that of the detector 6 employed in the first embodiment. Speaking in concrete terms, in contrast with a detection area of merely 30 mm$^2$ in the case of the detector 6, the detector 10 can have a detection area of 150 mm$^2$, a value five times as great. As a result, a residue analysis can be carried out with a high degree of sensitivity in comparison with that of the first embodiment.

It should be noted, however, that the shape of the detector 10 does not necessarily have to resemble a donut as described above. Instead, a detector having another structure can be employed as a substitute, so long as the detection area of its detecting device can be substantially increased. For example, a plurality of detectors 6 employed in the first embodiment are prepared and arranged to form a redial around the electron beam 1. As another alternative, the unit for accommodating the detector 6 in the housing 9 can be designed into a ring shape, wherein a plurality of detecting devices are laid out to form a circular structure. An essential feature offered by this embodiment is the fact that the detection area of the detecting device is substantially enlarged without obstructing the electron beam 1.

As described above, since this embodiment allows the reception area of the detector, to be enlarged in comparison with that of the first embodiment, it is possible to carry out a residue analysis with a high degree of sensitivity.

Embodiment 3

Figure 4:
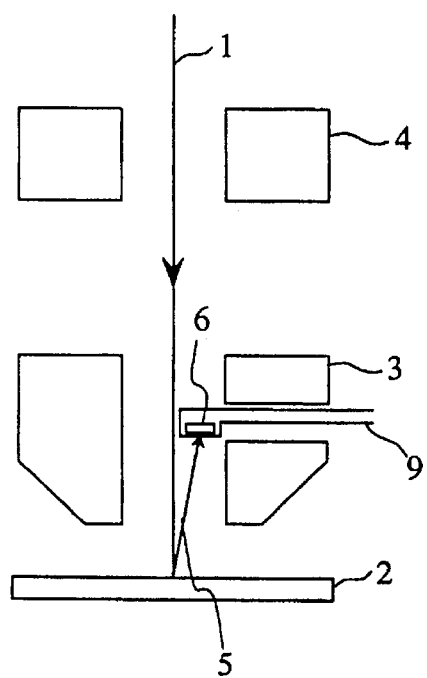
FIGS. 4, 5, 6 and 7 are cross-sectional model diagrams showing simplified configurations of still other embodiments, each implementing an X-ray analyzing apparatus in accordance with the present invention.

A still further embodiment of the present invention is shown in FIG. 4. In this embodiment, a detector 6 having an energy analyzing function is installed in an internal space inside an objective lens 3.

In this embodiment, a detector 6 having the same structure as that of the first embodiment is employed for detecting an X-ray. However, a detector 10 having a coaxial donut-like structure like the one employed in the second embodiment can also be used by installing it in an internal space inside the objective lens 3.

In this embodiment, the detector 6 can be installed at a position close to the sample 2 in comparison with the previous firsthand second embodiments, allowing an X-ray detection signal with a high intensity to be obtained. As a result, a residual analysis can be performed with a higher degree of sensitivity.

Embodiment 4

Figure 5:
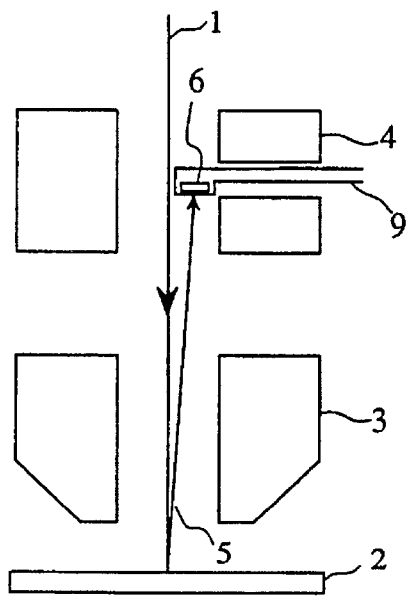

A still further embodiment of the present invention is shown in FIG. 5. In this embodiment, a detector 6 having an energy analyzing function is installed in an internal space inside a condenser lens 4.

In this embodiment, a detector 6 having the same structure as that of the first embodiment is employed for detecting an X-ray. However, a detector 10 having a coaxial structure like the one employed in the second embodiment can also be used by installing it in an internal space inside the condenser lens 4.

In this embodiment, the distance from the detector 6 to the surface of the sample 2 is long in comparison with the previous first to third embodiments. Accordingly, the intensity of the obtained X-ray detection signal is decreased slightly. With an increased distance from the detector 6 to the surface of the sample 2, however, an analysis of a sample with an angle θ smaller than that shown in FIG. 2, or a residue inside a fine hole with a a smaller diameter 2a, can thereby be carried out.

Embodiment 5

Figure 6:
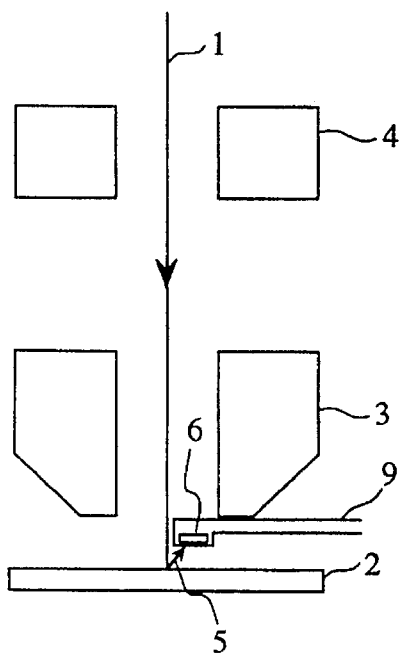

A still further embodiment of present invention is shown in FIG. 6. In this embodiment, a detector 6 is provided below an objective lens 3.

In this embodiment, the distance from the detector 6 to the surface of the sample 2 can be shortened in comparison with the previous first to third embodiments. Accordingly, an X-ray generated from the surface of the sample 2 experiencing no attenuation can be detected. As a result, a residual analysis can be performed with a high degree of sensitivity in comparison with the first to fourth embodiments.

Embodiment 6

Figure 7:
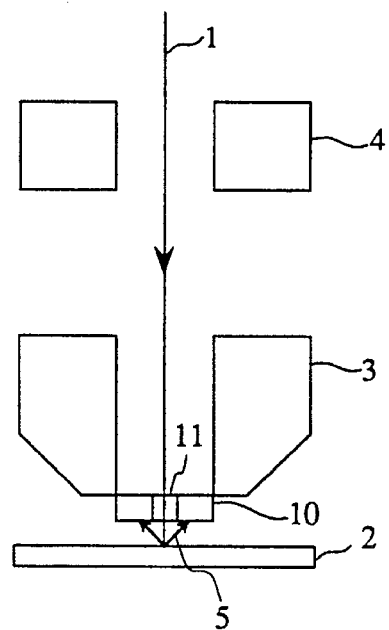

A still further embodiment of the present invention is shown in FIG. 7. In this embodiment, a donut-like X-ray detector 10 having a through hole 11 at the center thereof for passing an irradiated electron beam 1 is provided below an objective lens 3.

Much like the fifth embodiment, the distance from the surface of the sample 2 to the detector 10 in this embodiment can be shortened and, much like the second embodiment, the detection area of the detecting device can be enlarged. As a result, a residual analysis can be performed with a high degree of sensitivity in comparison with the first to fifth embodiments.

Embodiment 7

An analysis procedure for carrying out a quantitative analysis of the thickness of residue on the surface of a sample is explained through the description of this embodiment.

First of all, the beam current of an electron beam 1 is measured by using a measurement means such as a Faraday-cup collector provided inside an analyzing apparatus. Even though the means for measuring the beam current does not have to be installed at a particularly prescribed position, it is desirable to provide the means on a sample holder for holding a sample 2. Then, the position of residue on the surface of the sample 2 to be analyzed is determined by means of a secondary-electron detector 8. Finally, a quantitative analysis of the residue thickness is carried out in accordance with the method adopted in one of the first to sixth embodiments.

In the analysis methods and apparatuses implemented by the first to sixth embodiments described so far, one factor causing the accuracy of the residue-thickness analysis to deteriorate variation in beam current of the electron beam 1 due to a variety of reasons. Since the magnitude of an X-ray 5 generated from the surface of the sample 2 is proportional to the current density of the irradiated electron beam, the magnitude of the generated X-ray varies with changes in beam current. Accordingly, the residue thickness cannot be measured accurately.

In order to measure the residue thickness with a high degree of accuracy, it is thus necessary to clarify the relation between the current value of the electron beam and the detected-signal intensity of the X-ray 5. According to the measurement procedure of this embodiment, the detected-signal intensity of the X-ray 5 is measured after the measurement of the current value of the electron beam. Accordingly, information on the relation between the current value of the electron beam and the detected-signal intensity of the X-ray 5 can be obtained. As a result, the residue thickness can be measured with a high degree of accuracy by normalization (standardization) of the detected-signal intensity of the X-ray 5 with respect to the current value of the electron beam.

In the case of an analysis apparatus equipped with a position-measuring (position-monitoring) unit, memory and a drive-control mechanism at a sample stage thereof, the position of the instrument for measuring the current of the electron beam at the position of an instrument for carrying out a quantitative analysis of the sample or a plurality of such quantitative-analysis positions whenever applicable are stored in the memory. By moving the sample stage to any arbitrary position at a high speed, the measurement of the electron-beam current and the analysis of the sample surface can be carried out alternately with a high degree of efficiency.

As described above, this embodiment allows information on the electron-beam current and the detected-signal intensity of the X-ray 5 to be obtained accurately, and the residue thickness can hence be measured with a high degree of accuracy by normalization of the detected-signal intensity of the X-ray 5 with respect to the electron-beam current.

Embodiment 8

An analysis procedure for carrying out a quantitative analysis of the thickness of residue on the surface of a sample which is different from that of the seventh embodiment is explained through description of this embodiment.

First of all, the intensity of an X-ray generated from a reference sample, the material property of which is known in advance, is measured. Even though the reference sample does not have to be put at a particularly prescribed position, it is desirable to place the reference sample on a sample holder for holding a sample 2. Then, the position of residue on the surface of the sample 2 to be analyzed is determined by means of a secondary-electron detector 8. Finally, a quantitative analysis of the residue thickness is carried out in accordance with the method adopted in one of the first to sixth embodiments.

The seventh embodiment described above adopts an analysis method by normalization of the detected-signal intensity of the X-ray 5 with respect to the electron-beam current. On the other hand, according to this embodiment, the analysis method is implemented by normalization of the detected-signal intensity of the X-ray 5 with respect to the detector-signal intensity of the X-ray 5 generated by the reference sample. Also with the method of this embodiment, the same effects as those of the seventh embodiment can be obtained as well.

Embodiment 9

Measurement of the removed thickness of an underneath-layer material existing on the surface of the bottom of a hole resulting from a patterning process of a contact hole in a semiconductor manufacturing process is explained through description of this embodiment. In the measurement, the method of one of the first to eighth embodiments is adopted.

Figure 8:
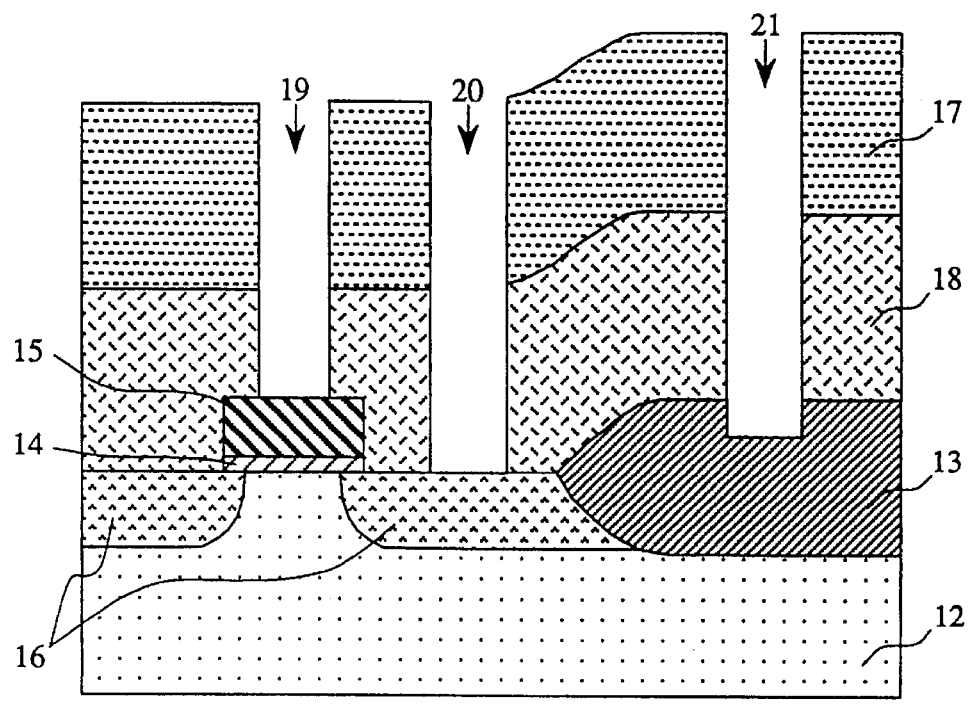
FIG. 8 is a cross-sectional diagram showing a typical structure of a contact hold in a semi-conductor device.

FIG. 8 is a diagram showing a cross section of a contact hole of a semiconductor device. Reference numeral 12 shown in the figure is a silicon substrate, whereas reference numeral 13 denotes an insulating film for element isolation. Reference numerals 14 and 15 are a gate insulating film and a gate electrode, respectively. Reference numeral 16 denotes a source and drain high-concentration layer, whereas reference numeral 17 is a resist layer. Reference numeral 18 denotes an interlayer insulating film, whereas reference numerals 19 and 20 are contact holes. Reference numeral 21 is a contact hole provided for evaluating the removed thickness of an underneath-layer material, the insulating film 13 for element isolation.

This embodiment is characterized in that a contact hole used for evaluating the removed thickness of the underneath-layer material is formed on a semiconductor device. The method adopted in one of the first to eighth embodiments is used for measuring the residue thickness of the element-isolation insulating film 13 existing on the surface of the bottom of the contact hole 21. From the difference between the original thickness of the element-isolation insulating film 13 before the patterning of the contact hole 21 and the thickness remaining after the contact-hole patterning, the removed thickness of the underneath-layer material can be derived.

Figure 9:
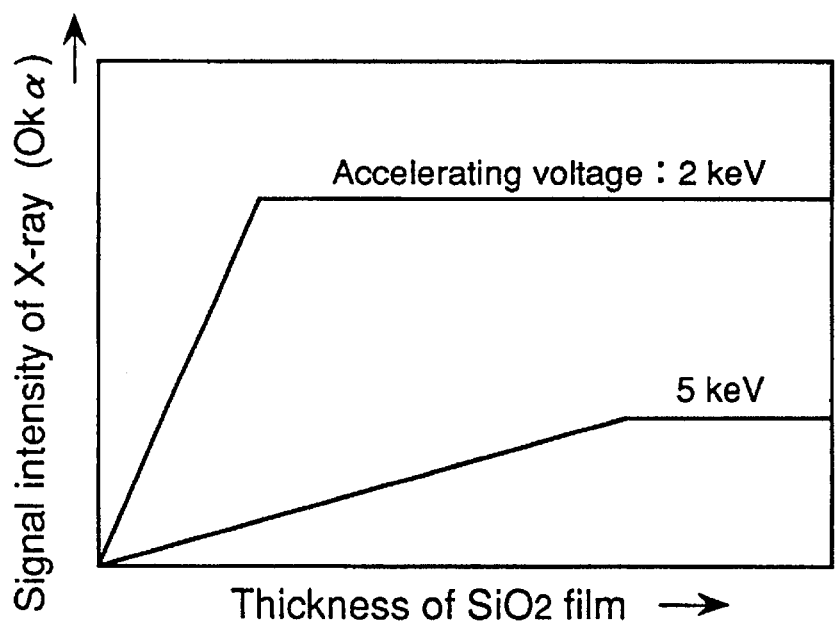
FIG. 9 is a diagram showing the dependence of the signal intensity of an X-ray on the $SiO_2$-film thickness.

A point to consider in the measurement of the residue thickness of the element-isolation insulating material 13 is that it is necessary to properly set the accelerating voltage of the electron beam according to the residue thickness. Dependence of the signal intensity of the X-ray on the thickness of the insulating film (the $SiO_2$ film) is shown in FIG. 9.

It is obvious from the figure that, for an accelerating voltage of 2 keV, the signal intensity of the X-ray is high but, on the other hand, for relatively high values of the $SiO_2$-film thickness, the signal intensity of the X-ray is saturated, making it impossible to measure the thickness of the $SiO_2$ film. For an accelerating voltage of 5 keV, on the other hand, the signal intensity of the X-ray is low but the thickness of a thicker $SiO_2$ film can be measured.

That the accelerating voltage varies inversely with the signal intensity of the X-ray can be attributed to the fact that the total amount of X-ray is a function of accelerating voltage. At an accelerating voltage of about three times the energy of the X-ray (about 0.5 keV in the case of an OK α X-ray), the total amount of X-ray reaches a maximum value. Refer to 'Optical Systems for Soft X-rays', written by A. G. Michette, Prenum Press, New York, 1986, pp. 22. It should be noted that as the accelerating voltage is raised to a value of higher than 5 keV, the signal intensity of the X-ray is decreased considerably, making it impossible to measure the residue thickness.

That, the accelerating voltage varies with the ability to measure the thickness of the $SiO_2$ film, is attributed to the fact that, the higher the accelerating voltage, the deeper the projection range of the electron into the film. For the reasons described above, it is necessary to lower the accelerating voltage to 2 keV in the case of a thin $SiO_2$ film and to raise the accelerating voltage to 5 keV in the case of a thick $SiO_2$ film.

As described above, according to this embodiment, a contact hole is formed for evaluating the removed thickness of an underneath-layer material on a semiconductor device. By measuring the residue thickness of the underneath-layer material on the surface of the bottom of the contact hole at an appropriate accelerating voltage, inline evaluation can be carried out for the removed thickness of the underneath-layer material.

Embodiment 10

A method for determining whether a contact hole in a semiconductor manufacturing process is a complete opening or not is described through this embodiment. In this embodiment, the method of one of the first to eighth embodiments is adopted.

Figure 16:
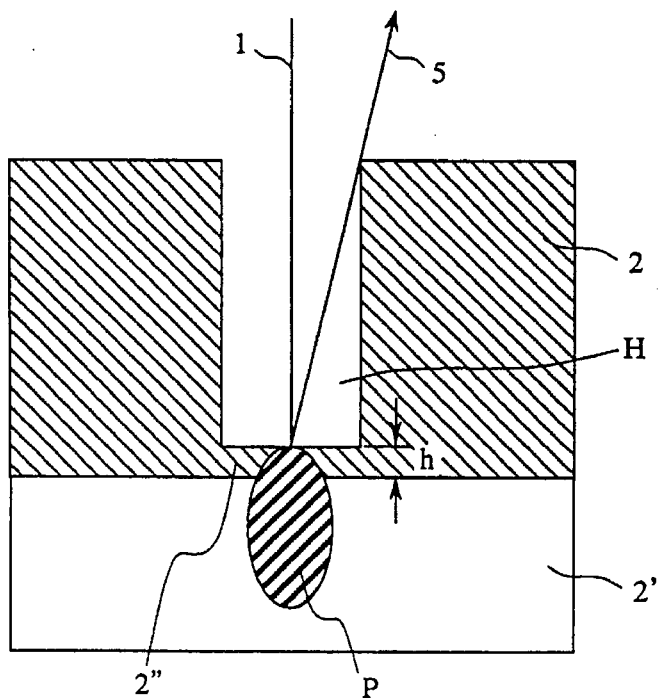
FIGS. 16 and 18 are cross-sectional model diagrams used for explaining techniques of judging the opening state of a contact hole by using an X-ray analysis method provided by the present invention.

FIG. 16 shows a state in which an analysis of $SiO_2$ residue existing on the surface of the bottom of a contact hole in a semiconductor device is carried out. As shown in the figure, a contact hole H is formed in an $SiO_2$ film 2 provided on a silicon substrate 2'. An $SiO_2$ residue 2" exists on the bottom of the contact hole H. An irradiated electron beam 1 with an accelerated voltage of 5 keV is applied to the $SiO_2$ residue 2".

Figure 17:
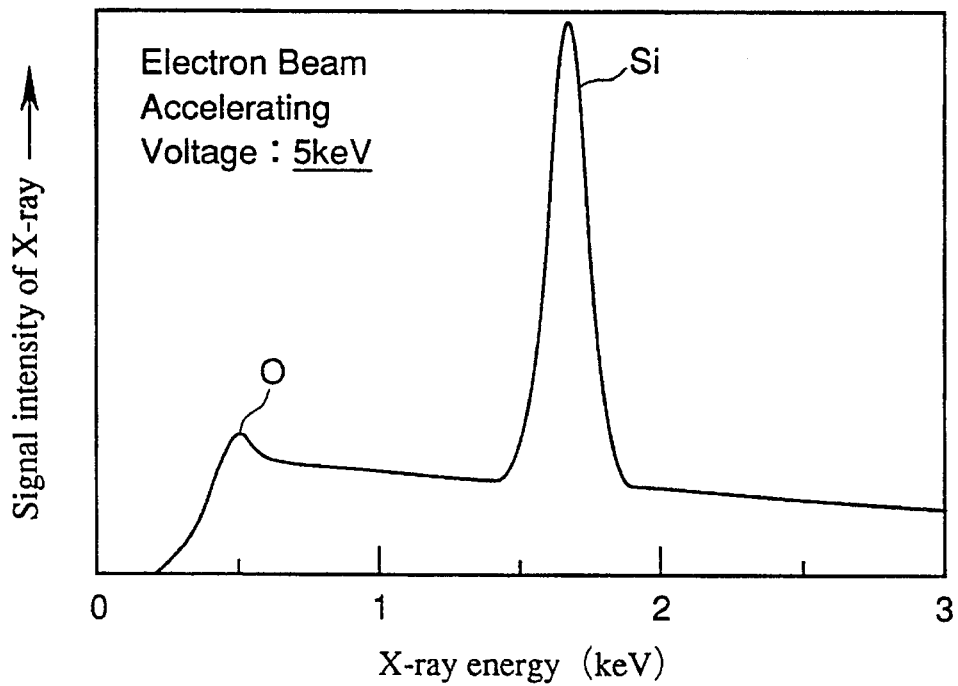
FIGS. 17 and 19 are charts representing spectra of X-rays detected by the techniques shown in FIGS. 16 and 18 respectively.

In the case of an $SiO_2$ residue 2" with a small thickness h, the electron beam 1 with an accelerated voltage of 5 keV allows irradiated electrons to penetrate the $SiO_2$ residue 2" with ease, arriving at the silicon substrate 2'. Accordingly, an area P generating X-rays 5 is distributed to deep locations in the silicon substrate 2'. In this case, the spectrum of the generated X-ray 5 is shown in FIG. 17. Since the X-ray generating area P has a portion in the silicon substrate 2' larger than a portion in the $SiO_2$ residue 2", the signal intensity of the Si (silicon) X-ray is high but, on the other hand, the signal intensity of the O (oxygen) X-ray from the $SiO_2$ residue 2" is low. For this reason, it is necessary to prolong the measurement time in order to determine the existence/non-existence of a thin $SiO_2$ residue.

In addition, for a high accelerating voltage of 5 keV, the amount of noise caused by the so-called 'bremsstrahlung' (braking radiation) is large, and X-rays generated from the sidewall (which is also an $SiO_2$ film) of the contact hole by electrons reflected from the surface of the bottom of the hole are also inevitably detected, lowering the precision of the analysis.

Figure 18:
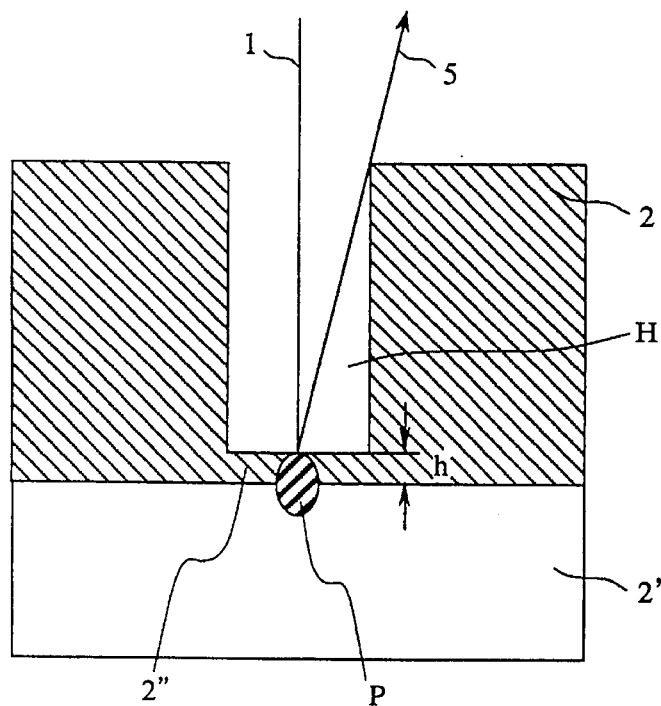
Figure 19:
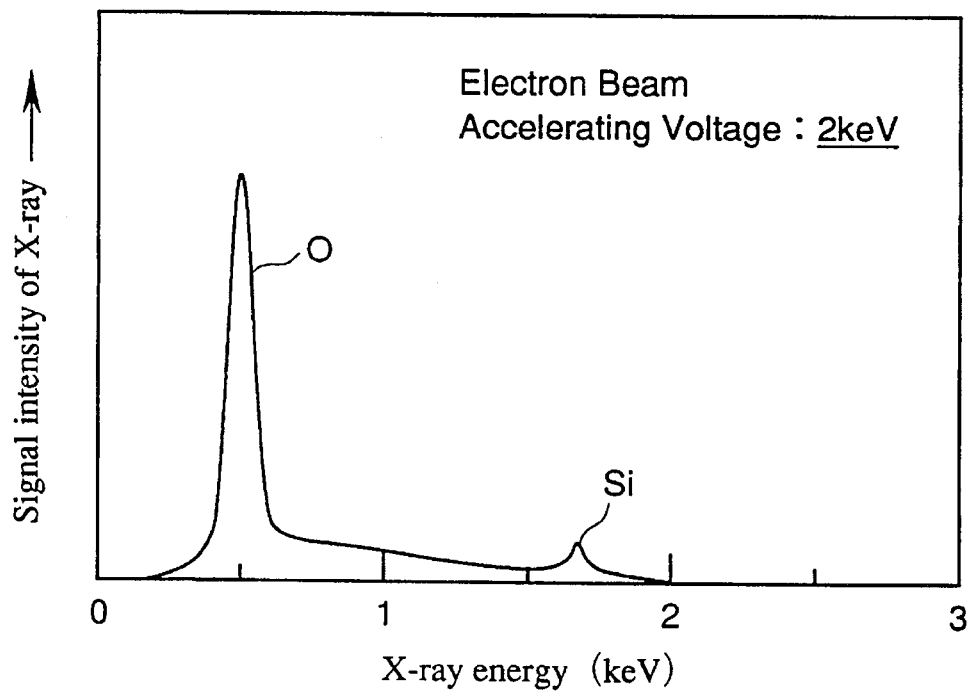

In the case of an electron beam with a low accelerating voltage of 2 keV, on the other hand, the distribution of the area P generating X-rays in the silicon substrate 2' is small in comparison with that for an accelerating voltage of 5 keV described above, as shown in FIG. 18. In this case, the spectrum of the generated X-rays is shown in FIG. 19. As described in the above ninth embodiment, the signal intensity of the O (oxygen) X-ray reaches a maximum value at an accelerating voltage of 1.5 to 2 keV. In this case, the signal intensity of the O (oxygen) X-ray is therefore high in comparison with that shown in FIG. 17.

In the case of an accelerating voltage of 2 keV, on the other hand, it is difficult to excite the Si (silicon) X-ray and, in addition, the distribution of the X-ray generating area P in the silicon substrate 2' is small. Accordingly, the signal intensity of the Si (silicon) X-ray is low.

Moreover, at a low accelerating voltage, the generation of reflected electrons and noise caused by the bremsstrahlung is low, allowing the amount of background noise to be reduced and the number of erroneous signals coming from the sidewall of the contact hole to be decreased. As a result, an analysis of an oxygen X-ray can be carried out with a high degree of sensitivity. For these reasons, it is possible to determine the existence/non-existence of $SiO_2$ residue on the surface of the bottom of the contact hole.

As described above, this embodiment allows an X-ray generated by light elements such as C (carbon) and O (oxygen) to be analyzed with a high degree of sensitivity if the X-ray analysis is carried out by accelerating an irradiated electron beam using a low accelerating voltage of 2 keV. As a result, it is possible to determine whether the opening of a contact hole is complete or not in a short period of time.

Embodiment 11

Figure 10:
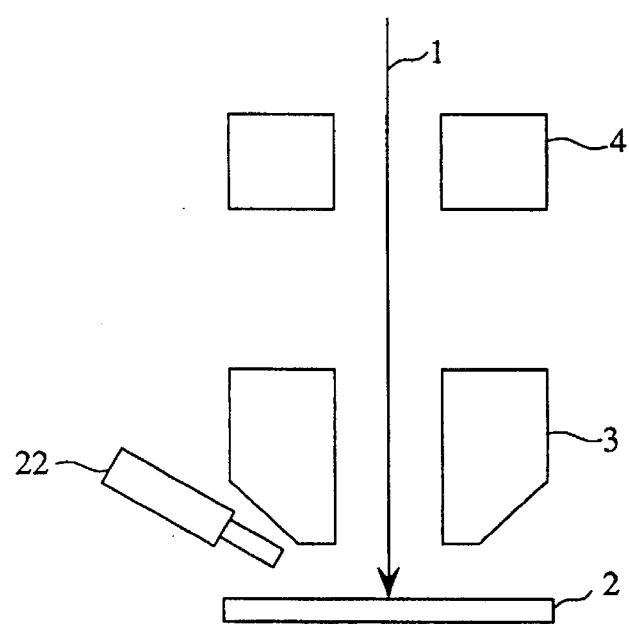
FIG. 10 is a cross-sectional model diagram showing a simplified configuration of a still further embodiment implementing an X-ray analyzing apparatus in accordance with the present invention.

A still further embodiment of the present invention is shown in FIG. 10. This embodiment is an example wherein a means for heating the surface of a sample 2 is provided. In this embodiment, an area on the surface of the sample 3, including a location to which an irradiated electron beam 1 is applied, is heated while the irradiated electron beam 1 is being applied to the location. In the meantime, residue on the surface of the sample 2 is analyzed by using the method adopted by one of the first to seventh embodiments. As a means for heating the surface of the sample 2, a semiconductor laser 22 having a wavelength of 800 nm is used for applying an irradiated laser light to the surface of the sample 2. In this way, an area on the surface of the sample 2 with a diameter of about 5 mm, to which the irradiated laser light is applied, is heated to a temperature of 200° C.

As the irradiated electron beam 1 is applied to the surface of the sample 2, a carbon compound is adhered to an area on the surface of the sample 2 to which the electron beam 1 is applied. If the intensity of an X-ray generated by the residue is low due to, for example, a small residue thickness, the sensitivity of analysis observed during the analysis of the residue on the surface of the sample 2 is low due to an effect of the adhered carbon compound. In order to analyze the thin residue with a high degree of sensitivity, it is thus necessary to prevent a carbon compound from being adhered to the surface of the sample 2 due to the application of the irradiated electron beam thereto. By heating the surface of the sample 2 to a temperature of 200° C. in accordance with this embodiment the adherence of a carbon compound to the surface of the sample 2 can be avoided, allowing the analysis of the residue to be carried out with a high degree of sensitivity even if the intensity of an X-ray generated from the residue is low.

In this embodiment, a semiconductor laser is used as a means for heating the surface of the sample It should be noted, however, that the means for heating the surface of the sample is not necessarily limited to a semiconductor laser. Any heating means can be used as long as it can substantially heat the surface of the sample. Note that, in order to prevent a carbon compound from being adhered to the surface of the sample, it is necessary to set the heating temperature of the surface of the sample at a value higher than 100° C.

A carbon compound can be prevented from being adhered to the sample surface by a technique other than heating the sample. More particularly, the means for generating an X-ray by application of an irradiated electron beam and the means for analyzing the generated X-ray are installed in a vacuum chamber. By getting the degree of vacuum in the vacuum chamber at $1 \times 10^{-6}$ torr or lower, the amount of the carbon compound existing in the vacuum chamber can be reduced, allowing the carbon compound to be prevented from adhering to the sample surface.

As described above, the carbon compound can be prevented from adhering to the surface of the sample by heating the surface of the sample in accordance with this embodiment, allowing residue to be measured with a high degree of sensitivity.

Embodiment 12

Figure 11:
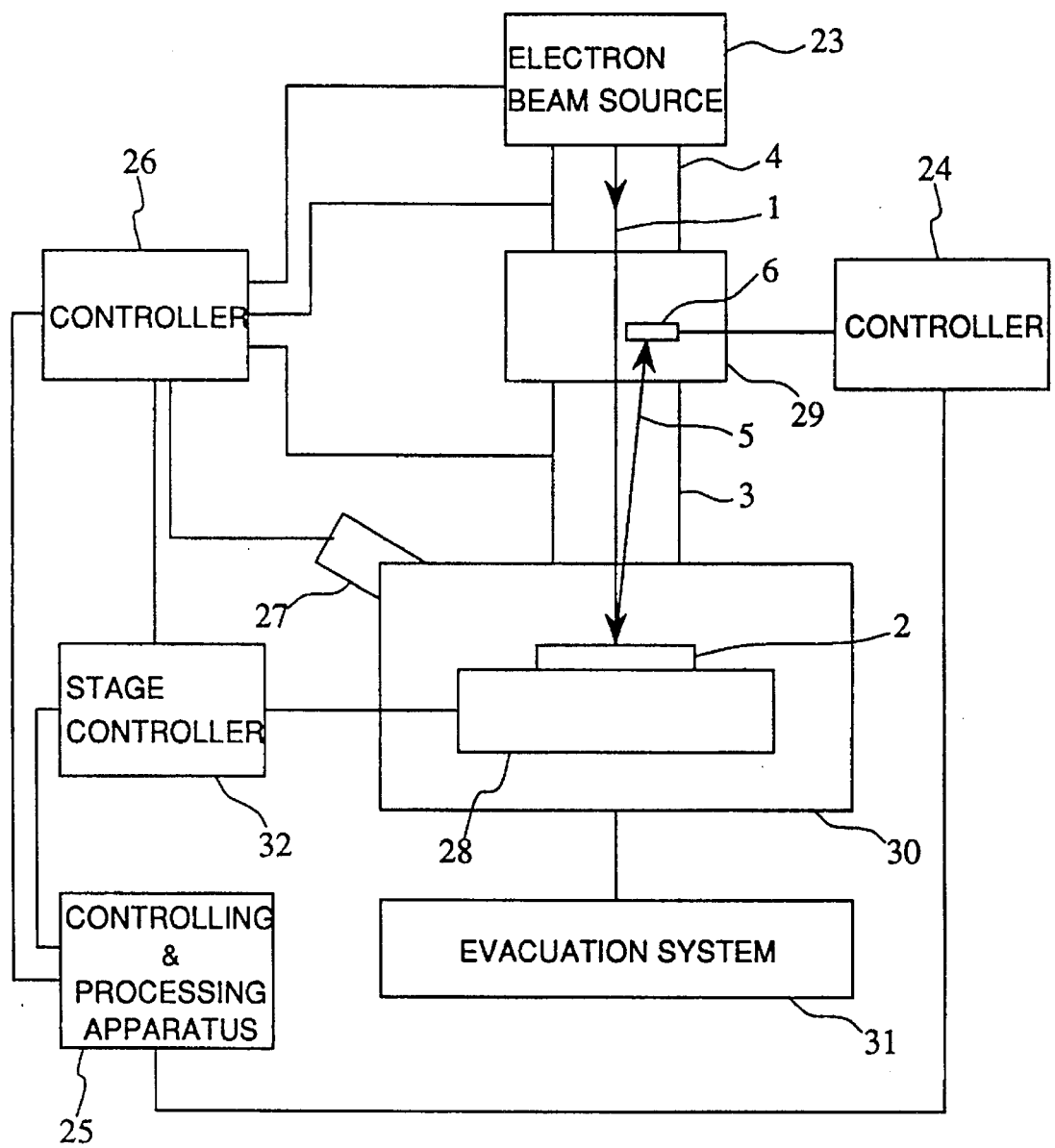
FIG. 11 is a cross-sectional model diagram showing a simplified configuration of a still further embodiment implementing an X-ray analyzing apparatus in accordance with the present invention.

The methods of analysis and apparatuses implemented by the first to tenth embodiments can be provided with additional functions to widen their generality as analysis apparatuses. For example, a function for measuring dimensions of a fine pattern (or a length measuring function) and a function for accelerating an electron beam to a high speed can be considered. An embodiment that includes these additional functions is shown in FIG. 11. As shown in the figure, accelerated electron beam 1 irradiated from an electron-beam source 23 is converged by a condenser lens 4 and an objective lens 3 before being applied to the surface of a sample 2 placed in a sample chamber 30. An X-ray 5 generated from the surface of the sample 2 by the application of the irradiated electron beam 1 thereto is detected by an X-ray detector 6 which has an energy analyzing function and is installed in a vacuum chamber 29. The X-ray detector 6 is installed at a position in a direction close to the center axis of the electron beam 1 when seen from a position on the surface of the sample 2 to which the irradiated electron beam 1 is applied. An X-ray detection signal output by the X-ray detector 6 is processed by a controller 24 before being transmitted to a controlling and processing apparatus 25 where analysis results are displayed.

In this embodiment, the accelerating energy of the electron beam 1 can be freely varied between 0.1 and 200 keV by using a controlling apparatus 26. In the case of an electron beam 1 with a low accelerating energy, a qualitative and quantitative analysis of residue on the surface of the sample 2 can be carried out by detecting an X-ray generated from the surface of the sample 2 as described above. For an electron beam 1 with a high accelerating energy of greater than 50 keV, on the other hand, an image on the surface of the sample 2 can be obtained by detecting secondary and reflected electrons coming from the surface of the sample 2. In particular, an electron with a high accelerating energy also has sufficiently high power to penetrate a substance. Thus, a shape inside a fine hole, for example, can be observed by detecting reflected electrons. These secondary and reflected electrons are detected by using an electron detector 27. As a result, not only can a shape inside the fine hole be observed, but it is also possible to identify the type of element making up the shape or the like.

The apparatus shown in FIG. 11 has an additional function for measuring the length of a fine pattern. Dimensions of a fine pattern are measured typically as described below. The surface of the sample 2 is scanned by the electron beam 1 by controlling a deflector provided in an objective lens 3 by means of the controlling apparatus 26. Secondary electrons generated from the surface of the sample 2 are detected to display a secondary-electron image of the surface of the sample 2 on a display screen of the controlling and processing apparatus 25. In this case, an electron beam 1 having an accelerating energy of smaller than 5 keV will work. A fine pattern, the dimensions of which are to be measured, is specified while the secondary-electron image is being observed. In this way, information on the dimensions of the fine pattern can be obtained from the amounts of deflection of the electron beam 1. Further, instead of deflecting the electron beam 1, a sample stage 28 can be moved by a stage controlling apparatus 32. The dimensions of the fine pattern can then be found as well from the amount of the movement.

It should be noted that the inside of an electron irradiating system for applying an irradiated electron beam 1 to the surface of the sample 2 and generating X-rays as well as secondary and reflected electrons therefrom, and the inside of a detecting system for detecting the generated X-rays as well as secondary and reflected electrons, are evacuated into a highly vacuum state by using an evacuating system 31.

As described above, this embodiment allows the shape of residue to be observed and dimensions of a fine hole to be measured in addition to a qualitative and quantitative analysis of the residue. As a result, more complete information on a fine pattern can be obtained.

The present invention has been explained by describing a variety of embodiments. In order to detect an X-ray more effectively, means for finely adjusting the positions of an optical element and a detector are required. Even though these adjusting means are not shown in the figures, position adjusting tremor structures can be installed if necessary. In addition, combinations of any of the embodiments cited above are also within the scope of the present invention. Furthermore, most of the means required for generating and measuring X-rays are installed in vacuum chambers even though they are not described in the explanations of the embodiments. It should be noted that, in case only few X-rays are absorbed by particles in the air, the sample can be put in a low-vacuum state.

It is obvious from the above description that, by virtue of the present invention, an X-ray generated from residue existing on the surface of a sample by the application of an irradiated and converged electron beam to the surface of the sample can be observed from a position in a direction close to the electron beam. As a result, a qualitative and quantitative analysis can be carried out on residue on the surface of a sample with large steps such as contact holes, to say nothing of a sample with small step. On top of that, the analysis is not destructive, allowing the sample to be returned back to the manufacturing process after the analysis.

It is further understood by those skilled in the art that the foregoing descriptions no more than a description of preferred embodiments of the disclosed method and apparatus and, therefore, a variety of changes and modifications may be made to the present invention without departing from the spirit and the scope thereof.

What is claimed is:

1. An X-ray analyzing method comprising the steps of:
    applying an irradiated electron beam converged by a condenser lens and an objective lens into a thin beam to the inside of a fine hole existing on a surface of a sample;
    observing X-rays generated from a residual substance existing inside said fine hole at the above step of applying said irradiated electron beam thereto; and
    performing a qualitative and quantitative analysis of said residual substance,
    said X-ray analyzing method characterized in that:
        said X-rays are observed by means of an X-ray detector having an energy analyzing function installed in an internal space of said condenser lens, an internal space of said objective lens or between said condenser lens and said objective lens; and
        only said X-rays radiated within the angular range $-\theta$ to $+\theta$ are detected by said X-ray detector, where $\theta$ is an angle formed with a center axis of said electron beam and so defined that $\tan\theta$ is substantially equal to a/d, and where a and d are the radius and the depth of said fine hole, respectively.

2. An X-ray analyzing method according to claim 1 characterized in that said X-ray detector has a donut-like structure having a through hole at the center thereof for passing said electron beam.

3. An X-ray analyzing method according to claim 1 characterized in that a beam current of said electron beam is measured prior to detection of said X-rays.

4. An X-ray analyzing method according to claim 1 characterized in that an X-ray analysis of a reference sample is performed prior to an analysis of said sample.

5. An X-ray analyzing method according to claim 1 characterized in that an area on said surface of said sample including a location, to which said irradiated electron beam is applied, is heated while said irradiated electron beam is being applied to said location.

6. An X-ray analyzing method according to claim 5 characterized in that said area is heated to a temperature of higher than 100° C.

7. An X-ray analyzing method according to claim 5 characterized in that said area is heated by applying an irradiated and converged optical beam to said area.

8. An X-ray analyzing method according to claim 7 characterized in that said optical beam is a visible light or an infra-red light.

9. An X-ray analyzing method according to claim 1 characterized in that said residual substance includes at least one of carbon atoms, oxygen atoms and silicon atoms.

10. An X-ray analyzing method according to claim 1 characterized in that said electron beam has energy capable of exciting at least one of carbon atoms, oxygen atoms and silicon atoms so as to generate X-rays.

11. An X-ray analyzing method according to claim 1 characterized in that said electron beam has an energy of smaller than 5 keV.

12. An X-ray analyzing method according to claim 1 characterized in that said electron beam has energy less than ten times energy of an X-ray to be observed.

13. An X-ray analyzing method comprising the steps of:
    applying an irradiated electron beam converged by a condenser lens and an objective lens into a thin beam to the inside of a fine hole existing on a surface of a sample;
    observing X-rays generated from a residual substance existing inside said fine hole at the above step of applying said irradiated electron beam thereto; and
    performing a qualitative and quantitative analysis of said residual substance,
    said X-ray analyzing method characterized in that:
        said X-rays are observed by means of an X-ray detector having an energy analyzing function installed between said objective lens and said sample; and
        only said X-rays radiated within the angular range $-\theta$ to $+\theta$ are detected by said X-ray detector, where $\theta$ is an angle formed with a center axis of said electron beam and so defined that $\tan\theta$ is substantially equal to a/d, and where a and d are the radius and the depth of said fine hole, respectively.

14. An X-ray analyzing method according to claim 13 characterized in that said X-ray detector has a donut-like structure having a through hole at the center thereof for passing said electron beam.

15. An X-ray analyzing method according to claim 13 characterized in that a beam current of said electron beam is measured prior to detection of said X-rays.

16. An X-ray analyzing method according to claim 13 characterized in that an X-ray analysis of a reference sample is performed prior to an analysis of said sample.

17. An X-ray analyzing method according to claim 13 characterized in that an area on said surface of said sample including a location, to which said irradiated electron beam is applied, is heated while said irradiated electron beam is being applied to said location.

18. An X-ray analyzing method according to claim 17 characterized in that said area is heated to a temperature of higher than 100° C.

19. An X-ray analyzing method according to claim 17 characterized in that said area is heated by applying an irradiated and converged optical beam to said area.

20. An X-ray analyzing method according to claim 19 characterized in that said optical beam is a visible light or an infra-red light.

21. An X-ray analyzing method according to claim 13 characterized in that said residual substance includes at least one of carbon atoms, oxygen atoms and silicon atoms.

22. An X-ray analyzing method according to claim 13 characterized in that said electron beam has energy capable of exciting at least one of carbon atoms, oxygen atoms and silicon atoms so as to generate X-rays.

23. An X-ray analyzing method according to claim 13 characterized in that said electron beam has an energy of smaller than 5 keV.

24. An X-ray analyzing method according to claim 13 characterized in that said electron beam has energy less than ten times energy of an X-ray to be observed.

25. An X-ray analyzing method comprising the steps of:
applying an irradiated electron beam converged by a condenser lens and an objective lens into a thin beam to the inside of a fine hole existing on a surface of a sample;
observing X-rays generated from a residual substance existing inside said fine hole at the above step of applying said irradiated electron beam thereto; and
performing a qualitative and quantitative analysis of said residual substance
said X-ray analyzing method characterized in that:
said X-rays are observed by means of an X-ray detector having an energy analyzing function installed in an internal space of said condenser lens, an internal space of said objective lens or between said condenser lens and said objective lens; and
only said X-rays radiated within the angular range −20 degrees to +20 degrees from a center axis of said electron beam are detected by said X-ray detector.

26. An X-ray analyzing method according to claim 25 characterized in that said X-ray detector has a donut-like structure having a through hole at the center thereof for passing said electron beam.

27. An X-ray analyzing method according to claim 25 characterized in that a beam current of said electron beam is measured prior to detection of said X-rays.

28. An X-ray analyzing method according to claim 25 characterized in that an X-ray analysis of a reference sample is performed prior to an analysis of said sample.

29. An X-ray analyzing method according to claim 25 characterized in that an area on said surface of said sample including a location to which said irradiated electron beam is applied is heated while said irradiated electron beam is being applied to said location.

30. An X-ray analyzing method according to claim 29 characterized in that said area is heated to a temperature of higher than 100° C.

31. An X-ray analyzing method according to claim 29 characterized in that said area is heated by applying an irradiated and converged optical beam to said area.

32. An X-ray analyzing method according to claim 31 characterized in that said optical beam is a visible light or an infra-red light.

33. An X-ray analyzing method according to claim 25 characterized in that said residual substance includes at least one of carbon atoms, oxygen atoms and silicon atoms.

34. An X-ray analyzing method according to claim 25 characterized in that said electron beam has energy capable of exciting at least one of carbon atoms, oxygen atoms and silicon atoms so as to generate X-rays.

35. An X-ray analyzing method according to claim 25 characterized in that said electron beam has an energy of smaller than 5 keV.

36. An X-ray analyzing method according to claim 25 characterized in that said electron beam has energy less than ten times energy of an X-ray to be observed.

37. An X-ray analyzing apparatus for performing a qualitative and quantitative analysis of a residual substance existing inside a fine hole on a surface of a sample by carrying out the steps of:
applying an irradiated electron beam converged by a condenser lens and an objective lens into a thin beam to the inside of said fine hole; and
observing X-rays generated from said residual substance at the above step of applying said irradiated electron beam thereto by means of an X-ray detector having an energy analyzing function,
said X-ray analyzing apparatus characterized in that said X-ray detector is installed in an internal space of said condenser lens, an internal space of said objective lens or between said condenser lens and said objective lens and within the angular range −θ to +θ, where θ is an angle formed with a center axis of said electronic beam and so defined that tan θ is substantially equal to a/d, and where a and d are the radius and the depth of said fine hole, respectively.

38. An X-ray analyzing apparatus according to claim 37 characterized in that said X-ray detector has a donut-like structure having a through hole at the center thereof for passing said electron beam.

39. An X-ray analyzing apparatus according to claim 37 characterized in that a means for measuring a beam current of said electron beam is provided therein.

40. An X-ray analyzing apparatus according to claim 37 characterized in that a means for performing an X-ray analysis of a reference sample is provided therein.

41. An X-ray analyzing apparatus according to claim 37 characterized in that a heating means is provided therein for heating an area on said surface of said sample including a location, to which said irradiated electron beam is applied, while said irradiated electron beam is being applied to said location.

42. An X-ray analyzing apparatus according to claim 41 characterized in that said heating means can heat said area to a temperature of higher than 100° C.

43. An X-ray analyzing apparatus according to claim 41 characterized in that said heating means is a means for applying an irradiated and converged optical beam to said area.

44. An X-ray analyzing apparatus according to claim 43 characterized in that said optical beam is a visible light or an infra-red light.

45. An X-ray analyzing apparatus according to claim 37 characterized in that said electron beam has energy capable of exciting at least one of carbon atoms, oxygen atoms and silicon atoms so as to generate X-rays.

46. An X-ray analyzing apparatus according to claim 37 characterized in that said electron beam has an energy of smaller than 5 keV.

47. An X-ray analyzing apparatus according to claim 37 characterized in that an evacuating means for evacuating space surrounding said sample to a vacuum state is provided therein.

48. An X-ray analyzing apparatus according to claim 47 characterized in that said evacuating means is capable of evacuating said space surrounding said sample to a vacuum state of lower than $1 \times 10^{-6}$ torr.

49. An x-ray analyzing apparatus according to claim 37, characterized in that at least a portion of said x-ray detector exposed to said electron beam is made of a non-magnetic material.

50. An X-ray analyzing apparatus for performing a qualitative and quantitative analysis of a residual substance existing inside a fine hole on a surface of a sample by carrying out the steps of:
applying an irradiated electron beam converged by a condenser lens and an objective lens into a thin beam to the inside of said fine hole; and
observing X-rays generated frown said residual substance at the above step of applying said irradiated electron beam thereto by means of an X-ray detector having an energy analyzing function,
said X-ray analyzing apparatus characterized in that said X-ray detector is installed between said condenser lens and said objective lens and within the angular range $-\theta$ to $+\theta$, where $\theta$ is an angle formed with a center axis of said electron beam and so defined that $\tan \theta$ is substantially equal to a/d, and where a and d are the radius and the depth of said fine hole, respectively.

51. An X-ray analyzing apparatus according to claim 50 characterized in that said X-ray detector has a donut-like structure having a through hole at the center thereof for passing said electron beam.

52. An X-ray analyzing apparatus according to claim 50 characterized in that a means for measuring a beam current of said electron beam is provided therein.

53. An X-ray analyzing apparatus according to claim 50 characterized in that a means for performing an X-ray analysis of a reference sample is provided therein.

54. An X-ray analyzing apparatus according to claim 50 characterized in that a heating means is provided therein for heating an area on said surface of said sample including a location, to which said irradiated electron beam is applied, while said irradiated electron beam is being applied to said location.

55. An X-ray analyzing apparatus according to claim 54 characterized in that said heating means can heat said area to a temperature of higher than 100° C.

56. An X-ray analyzing apparatus according to claim 54 characterized in that said heating means is a means for applying an irradiated and converged optical beam to said area.

57. An X-ray analyzing apparatus according to claim 56 characterized in that said optical beam is a visible light or an infra-red light.

58. An X-ray analyzing apparatus according to claim 50 characterized in that sand electron beam has energy capable of exciting at least one of carbon atoms, oxygen atoms and silicon atoms so as to generate X-rays.

59. An X-ray analyzing apparatus according to claim 50 characterized in that said electron beam has an energy of smaller than 5 keV.

60. An X-ray analyzing apparatus according to claim 50 characterized in that an evacuating means for evacuating space surrounding said sample to a vacuum state is provided therein.

61. An X-ray analyzing apparatus according to claim 60 characterized in that said evacuating means is capable of evacuating said space surrounding said sample to a vacuum state of lower than $1 \times 10^{-6}$ torr.

62. An x-ray analyzing apparatus according to claim 59, characterized in that at least a portion of said X-ray detector exposed to said electron beam is made of a non-magnetic material.

63. An X-ray analyzing apparatus for performing a qualitative and quantitative analysis of a residual substance existing inside a fine hole on a surface of a sample by carrying out the steps of:

applying an irradiated electron beam converged by a condenser lens and an objective lens into a thin beam to the inside of said fine hole; and observing X-rays generated from said residual substance at the above step of applying said irradiated electron beam thereto by means of an X-ray detector having an energy analyzing function, said X-ray analyzing apparatus characterized in that said X-ray detector is installed in an internal space of said condenser lens, an internal space of said objective lens or between said condenser lens and said objective lens and within the angular range $-20$ degrees to $+20$ degrees.

64. An X-ray analyzing apparatus according to claim 63 characterized in that said X-ray detector has a donut-like structure having a through hole at the center thereof for passing said electron beam.

65. An X-ray analyzing apparatus according to claim 63 characterized in that a means for measuring a beam current of said electron beam is provided therein.

66. An X-ray analyzing apparatus according to claim 63 characterized in that a means for performing an X-ray analysis of a reference sample is provided therein.

67. An X-ray analyzing apparatus according to claim 63 characterized in that a heating means is provided therein for heating an area on said surface of said sample including a location, to which said irradiated electron beam is applied, while said irradiated electron beam is being applied to said location.

68. An X-ray analyzing apparatus according to claim 67 characterized in that said heating means can heat said area to a temperature of higher than 100° C.

69. An X-ray analyzing apparatus according to claim 67 characterized in that said heating means is a means for applying an irradiated and converged optical beam to said area.

70. An X-ray analyzing apparatus according to claim 69 characterized in that said optical beam is a visible light or an infra-red light.

71. An X-ray analyzing apparatus according to claim 63 characterized in that said electron beam has energy capable of exciting at least one of carbon atoms, oxygen atoms and silicon atoms so as to generate X-rays.

72. An X-ray analyzing apparatus according to claim 63 characterized in that said electron beam has an energy of smaller than 5 keV.

73. An X-ray analyzing apparatus according to claim 63 characterized in that an evacuating means for evacuating space surrounding said sample to a vacuum state is provided therein.

74. An X-ray analyzing apparatus according to claim 73 characterized in that said evacuating means is capable of evacuating said space surrounding said sample to a vacuum state of lower thorn $1 \times 10^{-6}$ torr.

75. An x-ray analyzing apparatus according to claim 63, characterized in that at least a portion of said X-ray detector exposed to said electron beam is made of a non-magnetic material.

\* \* \* \* \*